United States Patent [19]

Turner et al.

[11] Patent Number: 4,882,013
[45] Date of Patent: Nov. 21, 1989

[54] APPLICATION OF TETRATHIAFULVALENES IN BIOELECTROCHEMICAL PROCESSES

[75] Inventors: Anthony P. F. Turner; Stuart P. Hendry; Marco F. Cardosi, all of Cranfield, England

[73] Assignee: Cranfield Institute of Technology, Cranfield, England

[21] Appl. No.: 18,046

[22] Filed: Feb. 24, 1987

[30] Foreign Application Priority Data

Feb. 27, 1986 [GB] United Kingdom ............... 8604830
Dec. 2, 1986 [GB] United Kingdom ............... 8628721

[51] Int. Cl.[4] ............................................. G01N 27/46
[52] U.S. Cl. ................................. 204/1 T; 204/403; 438/817
[58] Field of Search .................. 204/1 T, 403, 1 E; 435/817

[56] References Cited

U.S. PATENT DOCUMENTS

| 4,233,144 | 11/1980 | Pac et al. ........................ | 204/403 |
| 4,404,066 | 9/1983 | Johnson ........................... | 204/403 |
| 4,450,982 | 11/1985 | Hirai ................................ | 350/357 |
| 4,490,464 | 12/1984 | Gorton et al. ................... | 204/403 |
| 4,545,382 | 10/1985 | Higgins et al. .................. | 204/403 |

OTHER PUBLICATIONS

"The Development of Novel Biosensors" by W. John Albery et al. Presented at Biotech '85 (Europe): Online Publications, Pinner, United Kingdom, 1985, pp. 359-382 Soft-copy.

J. Electroanal. Chem. 194(1985) 211-222 Elsevier Sequoia S.A. Lausanne-Printed in The Netherlands, "Amperometric Enzyme Electrodes. PART I. Theory".

J. Electroanal. Chem. 194(1985) 223-235 Elsevier Sequoia S.A. Lausanne-Printed in the Netherlands, "Amperometric Enzyme Electrodes, PART II. Conducting Salts as Electrode Materials for the Oxidation of Glucose Oxidase".

"Electronic Properties of Electroactive Bilayer Lipid Membranes" by H. Ti Tien, Jan Kutnik, Pawel Krysinski and Z.K. Lojewska, Membrane Biophysics Lab, Dept. of Physiology, Mich. State U. pp. 149-167 soft-copy, NIH(GM-14971), Provost Office/MSU.

Primary Examiner—John F. Niebling
Assistant Examiner—Ben C. Hsing
Attorney, Agent, or Firm—Irell & Manella

[57] ABSTRACT

Bioelectrochemical processes use tetrathiafulvalenes (TTF) as a mediator of electron transfer between biological systems and electrodes. Typically it finds use in bioelectrochemical assays, e.g. involving glucose oxidase mediated oxidation of glucose. The TTF may be immobilized on the electrode surface, as may one or more enzymes involved in the process.

14 Claims, 8 Drawing Sheets

APPLICATION OF TETRATHIAFULVALENES IN BIOELECTROCHEMICAL PROCESSES

FIELD OF THE INVENTION

The present invention relates to the use of tetrathiafulvalene (TTF)

and its derivatives as mediator molecules in the transfer of electrons between redox systems and electrodes in bioelectrochemical processes. Such processes may be for example bioelectrochemical assay procedures, biological fuel cells and bioelectrosynthesis of chemicals.

BACKGROUND TO THE INVENTION

The electcrochemistry of oxidoreductases has received considerable attention in relation to applications in enzyme electrodes. See, e.g., A. P. F. Turner et al., *Biosensors* 1:85–115 (1985); F. W. Scheller et al., *Biosensors* 1:135–160 (1985); M. Mascini et al., *Biosensors* 2:147–172 (1985); and A. P. F. Turner and M. F. Cardosi, in *Biosensors: Fundamentals and Applications*, at pp. 257–275 (Eds. A. P. F. Turner, I. Karube and G. S. Wilson), Oxford: Oxford University Press, 1987. Many of the same considerations apply to their use in immunoassay and other enzyme-labelled assays e.g. DNA and RNA probe assays. In particular, highly efficient coupling of enzymic activity to the electrochemical detector is essential for sensitive and rapid assays. A number of approaches for the realisation of electron transfer from biological systems to amperometric electrodes have been described, but arguably the most effective is the use of low molecular weight mediators to shuttle electrons between the catalyst and an electrode. Various mediators that have been reported for use in enzyme electrodes, such as ferricyanide (P. Racine et al., *Experientia* 18:525–534 (1971)), tetracyano-p-quinodimethane (J. J. Kulys et al., *Biochim. Biophys. Acta.* 744:57–63 (1983)) and ferrocene (W. J. Aston et al., in *Charge and Field Effects in Biosystems*, at pp. 491–498 (Eds. M. J. Allen and P. N. R. Underwood), Tunbridge Wells, England: Abacus Press, 1984; A. E. G. Cass et al., *Anal. Chem.* 56:667–671 (1984); and A. P. F. Turner et al., *Anal. Chim. Acta.* 163:161–174 (1984) could also be useful in immunosensors.

Mediated enzyme-linked immunoassay, in which a GOD label was monitored using a ferrocene derivative, was first reported in 1985 by G. A. Robinson et al. in *Clin. Chem.* 31:1449–1452 (1985). A more elegant possibility is the use of the mediator molecule as a label. Weber et al. (*Analyt. Lett.* 12:1–9 (1979)) produced a conjugate of morphine and ferrocene carboxylic acid. They showed that the electrochemical oxidation of the ferrocene label was reduced when morphine antibody bound the conjugate and used this principle in a displacement assay for codeine (see (a) below). Since the key to practical oxidoreductase electrochemistry is the availability of a mediator such as ferrocene, it was apparent that this principle could be used to trigger an electrochemically coupled enzyme-catalysed reaction (see (b) below).

◯ = e.g. Codeine or morphine

The effective recycling of the ferrocene by GOD results in a further amplification of the signal over electrochemical noise due to electroactive substances present in the sample.

Electrochemically coupled enzyme reactions may also be activated by providing missing cofactors or coenzymes, as described by T. T. Ngo et al., *Appl. Biochem. Biotechnol.* 11:663–670 (1985). Quinoprotein dehydrogenases could prove particularly valuable in this respect.

An immunoassay for prostatic acid phosphatase (PAP), a prostate tumor marker from human serum, which relies on enzyme amplification is shown below. See M. F. Cardosi et al., "An Electrochemical Immunoassay Using Enzyme Amplification", in *Second International Meeting on Chemical Sensors* (Eds. J. L. Acoutrier et al.), 1985.

The catalytic activity of the enzyme label (alkaline phosphatase) used in a sandwich assay is monitored by the addition of the substrate $NADP^+$ leading to the formation of the dephosphorylated product $NAD^+$. The $NAD^+$ formed enters a redox cycle involving the enzymes alcohol dehydrogenase and diaphorase leading to the reduction of a mediator (ferricyanide). Electrons from the $NAD^+/NADH$ redox cycle passed via the diaphorase to the $Fe_{III}(CN)_6/Fe_{II}(CN)_6$ couple. The reduced species $FE_{II}(CN)_6$ was reoxidised at a platinum electrode at 450 mV versus a saturated calomel electrode producing an amperometric response.

Similar principles may be applied to other affinity reactions such as DNA and RNA probe assays.

Amperometric enzyme electrodes have been investigated in which the electrode has a conductive surface comprising an organic solid with metal-like electrical conductivity ("organic metal"). These substances are formed as charge-transfer complexes between an electron donor molecule and an electron acceptor molecule. The principal investigations have been with 7,7,8,8-tetracyanoquinodimethane (TCNQ) as electron acceptor and N-methyl-phenazinium (NMP) as electron donor, but the possibility of $TTF^+$ $TCNQ^-$ complexes has also been considered. See J. J. Kulys, *Biosensors* 2:3–13 (1986). However, the present invention is dealing with the use of TTF in a different context; uncomplexed, as a mediator of electron transfer.

SUMMARY OF THE INVENTION

According to one aspect of the present invention there is provided a bioelectrochemical process involving electron transfer between a redox system and an electrode, characterised in that said electron transfer is mediated by a tetrathiafulvalene, not being an "organic metal" complex. The TTF is preferably deposited on the electrode, but may be in solution. An oxidoreductase enzyme may be immobilised on the electrode. The invention also includes assay procedures incorporating such processes, and TTF-modified electrodes for use in the processes.

BRIEF DESCRIPTION OF THE DRAWINGS

Further features of the invention will be described with reference to the accompanying drawings, wherein.

DETAILED DESCRIPTION

Figure 1:
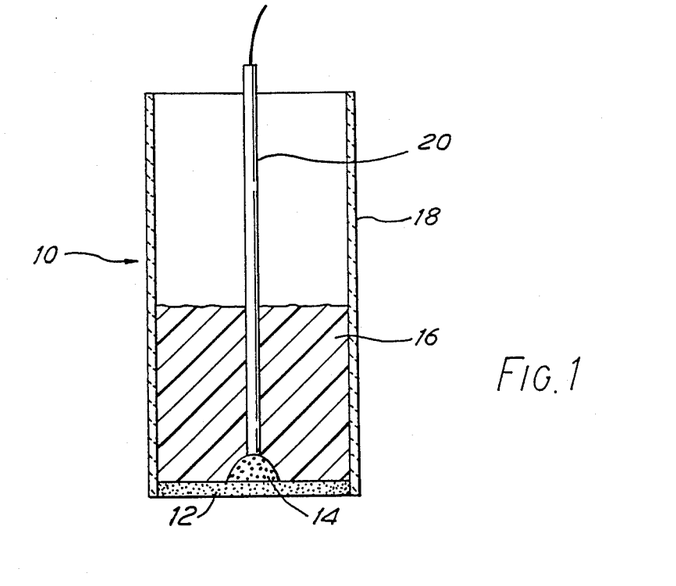
FIG. 1 shows a diagrammatic cross-sectional side view of an electrode.

Construction of Electrode (A) As shown in FIG. 1 an electrode 10 is shown held in place by support 16. The electrode is constructed from a 6.0 mm diameter graphite foil disc 12 which is cemented to 3.0 cm length of precut soda glass tube 18, 7.0 mm in diameter, using epoxy resin (Araldite - Trade Name). The resin is allowed to harden for 20 minutes at 100° C. A 6 cm length of insulated wire 20 is attached to the back of the graphite foil 12 with silver loaded epoxy resin 14 (Araldite) and left to set for 20 minutes at 100° C.

(B) 10 mg of TTF (FLUKA) were added to 1 ml of acetone and allowed to dissolve. The electrode 10 was placed in this solution and left at 30° C. for two hours. After this time the electrode was removed and left to air dry for 60 minutes at room temperature.

(C) The electrode 10 was transferred to a solution of 20 mg/ml 1-cyclohexyl-3(2-morpholinoethyl) carbodiimide metho-p-toluene sulphonate (Sigma Chemical Company) in 0.5 M citrate buffer pH 5.5 for 90 minutes at room temperature. This is a bifunctional ligand to aid immobilisation of the enzyme on the electrode through covalent bonding between carboxyl and amino groups. The electrode was rinsed thoroughly in distilled water before being placed in 25 mg/ml glucose oxidase solution (EC 1.1.3.4, Sturge Biochemicals) in 20 mM carbonate buffer pH 9.5 at room temperature for 60 minutes. The electrode was rinsed in 20 mM phosphate buffer pH 7 and was ready to use.

The results given below are derived from averaging the output of five electrodes constructed and prepared as above. The output of the different electrodes can vary considerably and will depend to some extent on the surface area. However, careful construction can increase the consistency between electrodes.

Apparatus

The sensors were operated using a BBC 32K microcomputer via a programmable biosensor interface (Artek, Lavendon, Bucks., England) (see Turner et al., *Biosensors* 1 (1985), supra, and Turner et al., *Anal. Chim. Acta* (1984), supra). This system utilised a Ag/AgCl reference electrode. A three electrode configuration was also employed for temperature profile and current potential curve determination. A saturated calomel electrode was used as a reference and the auxiliary electrode was 0.46 mm diameter platinum wire.

The sensors were immersed in 15 ml of buffer (usually 20 mM phosphate buffer pH 7.0), contained in a 20 ml glass water-jacketed cell thermostatted at 25±0.5° C. Unless stated otherwise, the sensors were poised at 200 mV versus Ag/AgCl or 160 mV versus saturated calomel electrode.

Buffers and Reagents

The standard buffer was 20 mM sodium phosphate pH 7.0 containing 0.1 M KCl.

The buffers used for the pH profiles contained 0.1 M KCl and were as follows:

pH 4.0, 20 mM citric acid-Na$_2$HPO$_4$
pH 4.4, 20 mM citric acid-Na$_2$HPO$_4$
pH 5.0, 20 mM citric acid-Na$_2$HPO$_4$
pH 5.8, 20 mM sodium phosphate
pH 6.3, 20 mM sodium phosphate
pH 7.0, 20 mM sodium phosphate
pH 7.5, 20 mM sodium phosphate
pH 8.0, 20 mM sodium phosphate
pH 9.4, 20 mM sodium carbonate Buffers used in the three electrode system lacked 0.1 M KCl. Glucose was introduced into the system by injection of known volumes of 1.0 M D-glucose which had been stored overnight to allow equilibration of $\alpha$- and $\beta$-anomers. All chemicals were of analytical grade.

Calibration of the Enzyme Electrode

Figure 2:
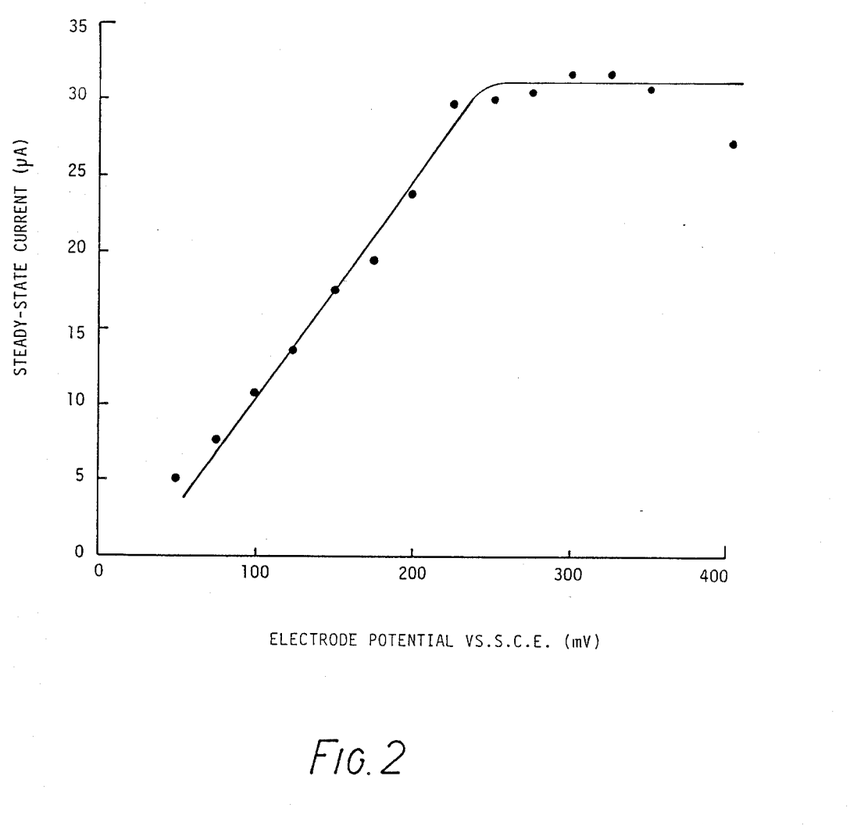
FIG. 2 is a graph showing current potential response of a TTF-modified glucose oxidase electrode.

The current voltage response obtained for the TTF modified glucose oxidase (GOD) electrodes is shown in FIG. 2. This was obtained by subtracting the currents given by the electrode in the absence of glucose from currents given by the electrodes in the presence of glucose, at various operating potentials. The plateau region from 220 to 400 mV concurs with other unreported data obtained from direct current cyclic voltammetry of TTF. It was at potentials near the lower end of this region that the electrodes were operated, thus minimising the effect of small fluctuations in the reference potential, whilst also minimising the amount of enzyme-independent oxidation of redox species present in samples. Control electrodes lacking TTF or GOD gave no current in response to glucose.

Figure 3:
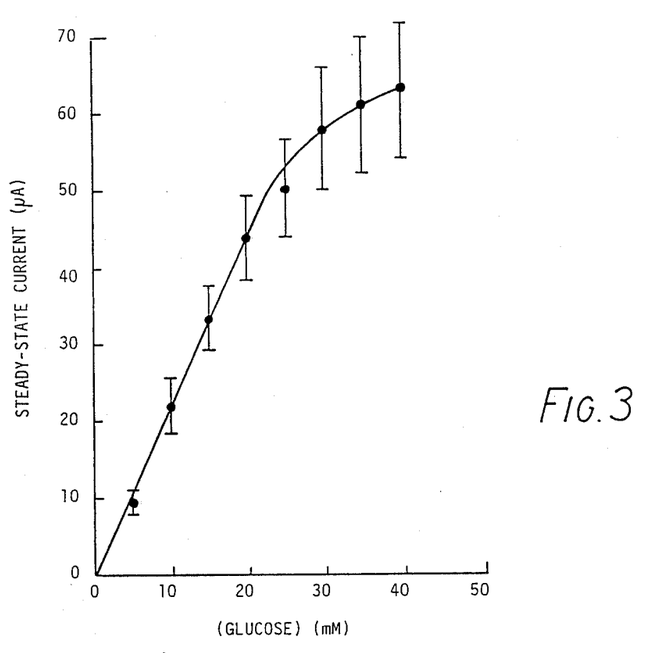
FIG. 3 is a graph showing a calibration curve of steady state current versus glucose concentration for a TTF-modified glucose oxidase electrode.

The electrodes gave a linear steady-state current response in the range of 0 to 25 mM (FIG. 3). Above 25 mM the calibration curve became non-linear saturating at 70 mM glucose. This was consistent with previous results using ferrocene (See Cass et al., Anal. Chem. cited supra) and was considered to be a reflection of the inherent enzyme kinetics of the immobilised glucose oxidase under these conditions. The response of the electrode to glucose was rapid; the electrodes typically took 3 to 5 minutes to reach a steady-state current, 90% of this response being achieved 60 to 90 seconds after the glucose addition. The standard deviation error bars shown in FIG. 3 for measurements from five different electrodes indicate the reproducibility afforded by this simple fabrication technique.

pH Profile of Enzyme Electrodes

Figure 4:
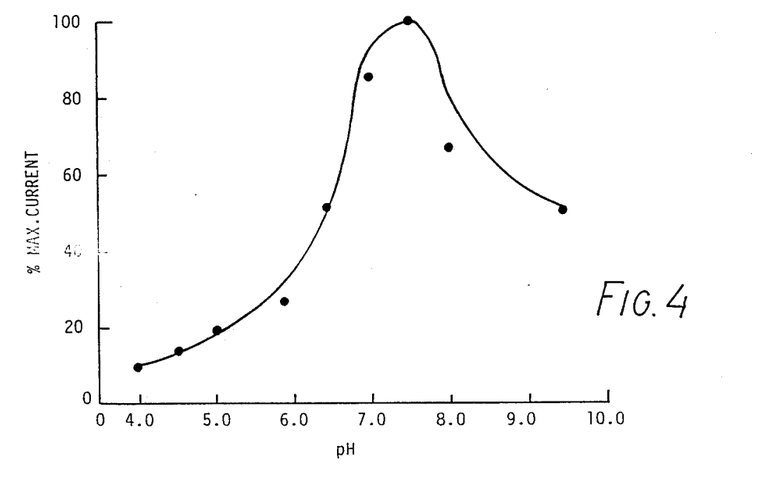
FIG. 4 is a graph showing a pH profile of the TTF-modified glucose oxidase electrode.

The effect of pH on the anodic current of the electrode was investigated over the range, pH 4.0 to 9.4 (FIG. 4). The data in FIG. 4 is expressed as a percentage of the current at pH 7.5 to reduce the error between electrodes of different initial activity. The electrodes demonstrated an optimum at pH 7.5. This result is in agreement with data published for the use of glucose oxidase with other artificial electron acceptors (R. M. Ianiello et al., *Anal. Chem.* 53:2090-2095 (1981); Y. A. Aleksandrovskii et al., *Biokhimiya* 46:708-716 (1981)), compared to the pH optimum 5.5 to 5.7 when oxygen is the electron acceptor (R. Bentley, *The Enzymes*, 2nd Ed., Vol. 7, at pages 567-576 (Eds. P. D. Boyer, H. Lardy and K. Myrback), 1983). TTF replaces oxygen in the native reaction, this greatly reducing the production of hydrogen peroxide. This results in an excess of protons in close proximity to the enzyme making the microenvironment of the enzyme become more acidic and producing an apparently more basic pH optimum for the enzyme. The extremes of the pH range gave rise to denaturation of the enzyme electrode.

The Effect of Temperature on the Enzyme Electrode

Figure 5:
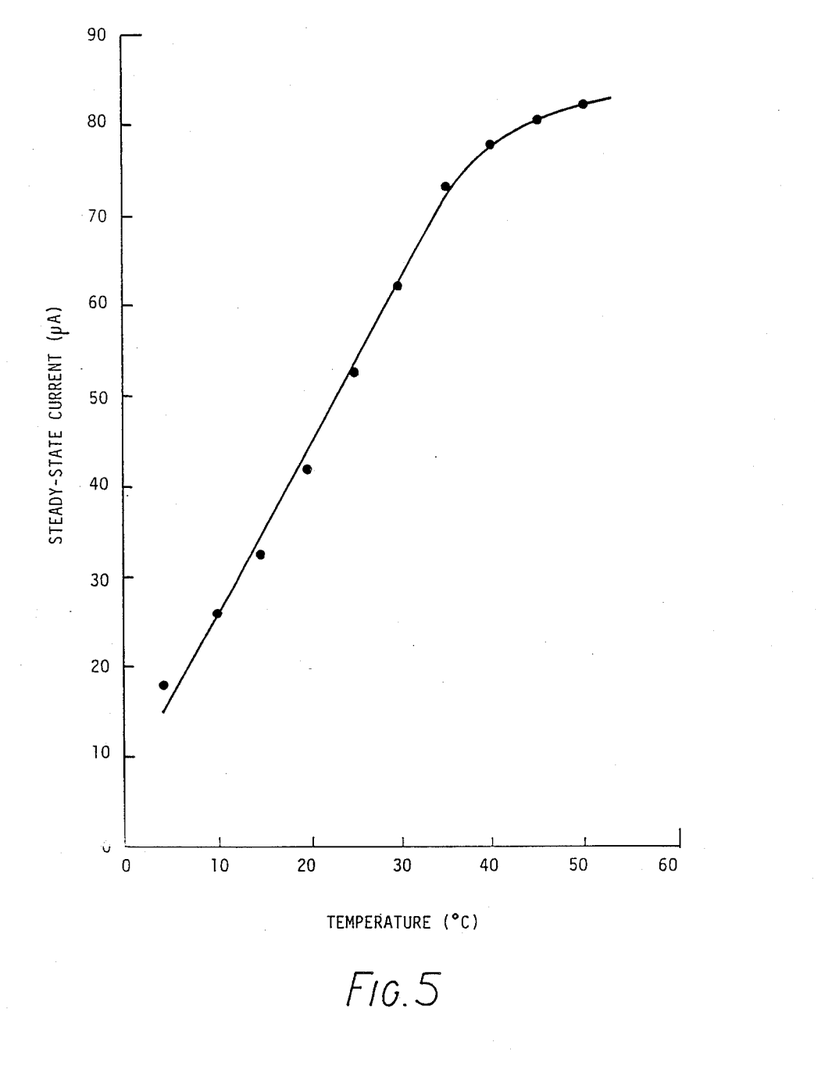
FIG. 5 is a graph showing temperature response of the TTF-modified glucose oxidase electrode.

This effect of temperature on the electrode was investigated between 4° to 50° C. FIG. 5 shows the typical increase of an electrode's steady-state current in response to increasing temperature, at saturating glucose concentrations (80 mM). Within the linear portion of the graph there was an average increase of 1.8 $\mu$A/°C. Above 35° C. the plot ceased to be linear due to thermal denaturation of the enzyme electrode. When maintained at temperatures above 35° C. the current fell rapidly, this effect being more severe at higher temperatures.

The Effect of Oxygen on the Enzyme Electrode

Figure 6:
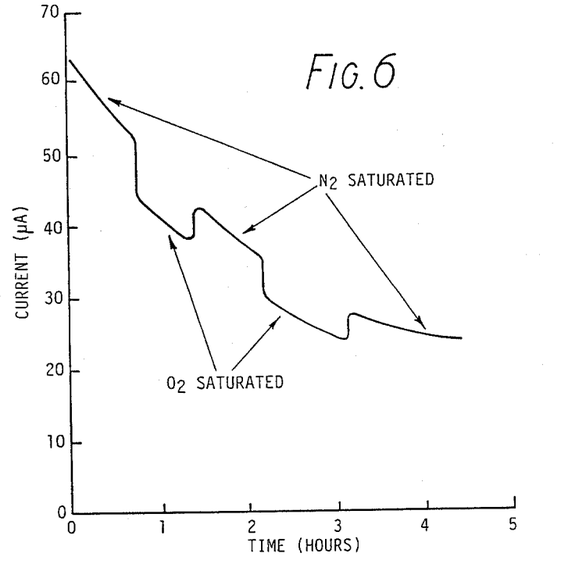
FIG. 6 is a graph showing the effect of nitrogen and oxygen saturation on the anodic current of a typical TTF-modified glucose oxidase electrode, at saturating glucose concentration.

FIG. 6 is a graph showing the effect of nitrogen and oxygen saturation on the anodic current of a typical TTF-modified glucose oxidase electrode, at saturating glucose concentration (Glucose=100 mM).

Peak currents achieved from the electrodes when operating in oxygen-saturated buffer were 15.1%±5.96% (n=5) lower than the peak currents obtained in nitrogen saturated buffer. The electrodes were poised at a low potential (200 mV versus Ag-/AgCl) and any $H_2O_2$ produced would not have been oxidised by the electrode. The oxygen interference effect was the result of competition between TTF and oxygen for electrons from the reduced enzyme, highlighting the need for a mediator to have a high affinity for electrons and fast electron transfer kinetics. When the electrodes were operated in air saturated buffer the reduction in current due to oxygen in the air was less than 5%. Under normal operating conditions, therefore, oxygen interference would be negligible.

Stability of the Electrodes

Figure 7:
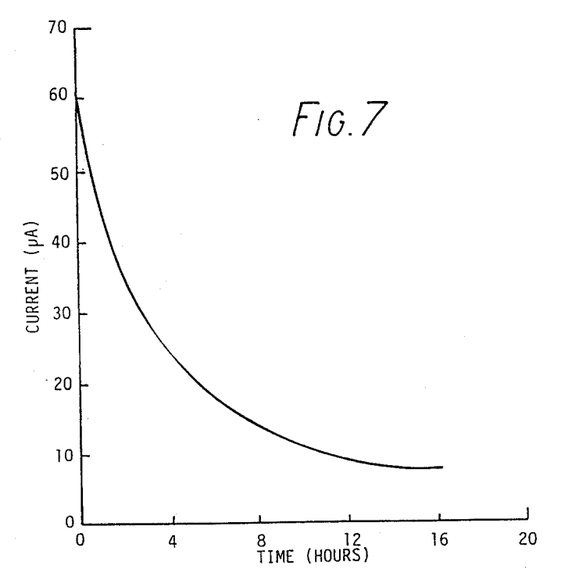
FIG. 7 is a graph showing the decay of a typical TTF-modified glucose oxidase electrode at saturating glucose concentration.

FIG. 7 is a graph showing the decay of a typical TTF-modified glucose oxidase electrode at saturating glucose concentration (Glucose=100 mM).

When fresh electrodes were run under saturating glucose concentrations (80 mM) the peak current had a half-life of 1.5 to 2 hours. The peak current eventually fell to a steady level after ca. 12 hours. This was not due to consumption of the glucose by glucose oxidase, since further additions of glucose did not give rise to higher currents. When transferred to fresh buffer containing 80 mM glucose, however, up to 35% of the original activity could be regained. When this process was repeated with the same electrodes similar results were obtained. These preconditioned electrodes responded to glucose additions after 20 hours of operation, giving 25.4%±2.9% (n=5) of the original current response. Enzyme electrodes were stored in 20 mM phosphate buffer pH 7.0 at 4° C. for 5 weeks. After this time the electrodes produced normal responses to additions of glucose. The currents achieved from the electrodes were 26.9%±3.8% (n=6) of the currents given by fresh electrodes.

TTF-modified Glucose Dehydrogenase

The usefulness of TTF with a dehydrogenase, quinoprotein glucose dehydrogenase (EC 1.1.99.17) was studied. This NAD-independent glucose dehydrogenase is of particular interest to biosensor work as oxygen does not play a role in its native reaction, thus it is less susceptible to changes in oxygen tension than glucose oxidase.

The base electrodes were constructed and set up as described previously. A standard dialysis membrane was boiled in 1% EDTA for 15 minutes and then thoroughly washed in purified water. The TTF modified electrodes were washed in 20 mM acetate buffer, pH 5.5, and concentrated glucose dehydrogenase isolated from *Acinetobacter calcoaeticus* (50 μl) was applied to the surface of the electrode and was retained behind a piece of prepared dialysis membrane by a rubber O-ring. Calibration of the electrode was performed as usual.

Figure 8:
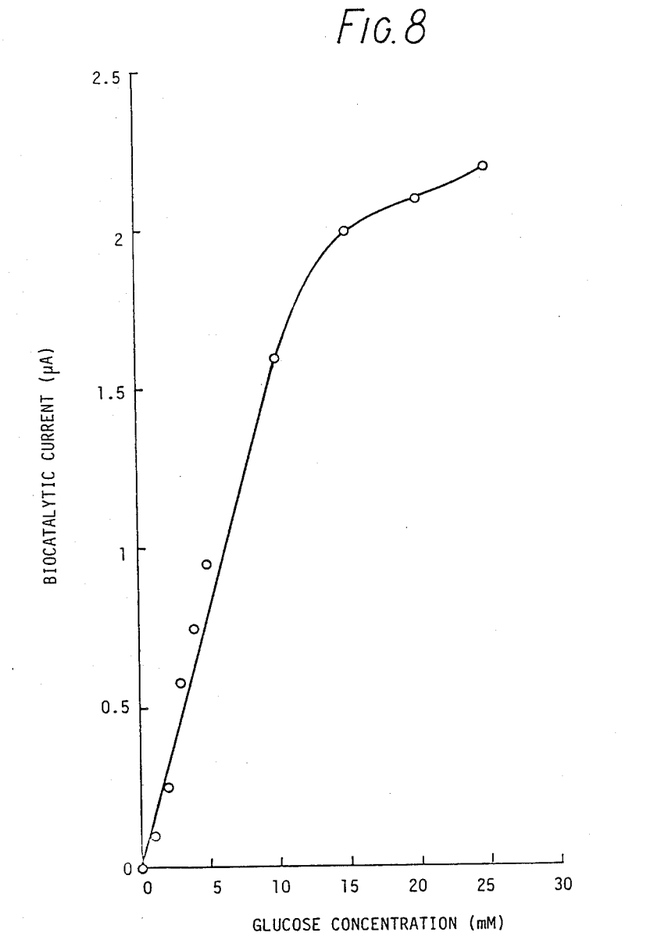
FIG. 8 shows a calibration curve of a membrane-entrapped glucose dehydrogenase TTF-modified electrode.

As shown in FIG. 8, the electrode gave a linear steady-state current response in the range 0-10 mM. Above this value the calibration curve became non-linear saturating at ca. 50 mM. Thus, glucose/TTF will readily transfer electrons from glucose dehydrogenase.

The Use of TTF with L-amino-acid Oxidase as an L-amino-acid sensor

Preliminary experiments were also performed on an L-amino acid sensor using TTF as a mediator. L-amino acid sensors were constructed essentially as described by J. M. Dicks et al., in *Analyt. Chim. Acta.* 182:103–112 (1986), with the exception that TTF was used as an immobilised mediator in the place of ferrocene. On addition of 500 μl of 1 M L-glutamic acid a mean increase in anodic current of 15 μA was observed. These results suggest that L-amino acid oxidase is compatible with TTF as a mediator.

Electron Transfer from Glucose Oxidase to a Graphite Electrode in Aqueous Solution TTF is extremely insoluble in water. It is this property which allows it to be readily entrapped at an electrode surface when used in buffered solution. It is, however, sometimes desirable to use mediators in aqueous solution, for example to investigate the kinetics of electron transfer from enzymes to mediators or for use in electrochemical enzyme amplification and labelling systems.

40 mg of TTF was dissolved in 1 ml of Tween-20 (Trade Mark). This solution was made up to 100 ml with 20 mM sodium phosphate buffer, pH 7.0. A three electrode system as previously described was employed with the addition of a potential ramp generator. A 5 mm diameter glassy carbon working electrode and a platinum counter electrode were used, with a saturated calomel electrode as reference. The experiment was performed at 25° C. 15 ml of 20 mM phosphate buffer, pH 7.5 was placed in to the reaction cell: to this was added 300 μl of the TTF solution and 300 μl of 1 M glucose. Linear sweep voltametry (L.S.V.) at a sweep rate of 4.5 mV/sec was then performed. Once this was complete 300 μl of 20 mg/ml glucose oxidase solution was added and the L.S.V. repeated.

Figure 9:
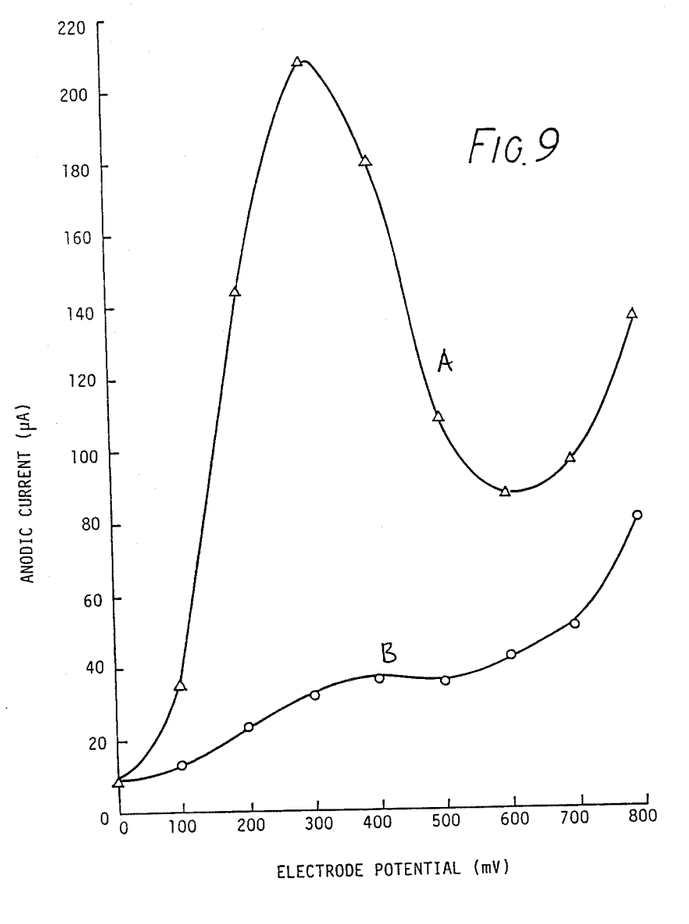
FIG. 9 shows a linear sweep voltammogram of solubilised TTF and glucose with (curve A) and without (curve B) glucose oxidase.

As can be seen from FIG. 9 significant electron transfer from the glucose oxidase to the electrode via TTF was achieved. The catalytic peak was observed at ca. 220 versus S.C.E. which corresponds with the oxidation peak of TTF determined by cyclic voltametry.

Sensor with Improved Enzyme Immobilisation

Owing to the relative instability of the carbodiimide immobilised electrodes, the lifetime of the electrodes can be improved with a superior immobilisation method. Glucose oxidase is a glycoenzyme (containing 16% carbohydrate) which offers the opportunity to link enzyme molecules together and to an electrode via its carbohydrate chains rather than through amino acid residues. See Barbaric et al., *Third Eur. Conqr. Biotechnol.* 1:307–213 (1984).

The base electrodes were constructed as described previously and a three electrode system was employed exactly as before.

100 mg of glucose oxidase (Sturge) (EC 1.1.3.4) was dissolved with 10 mg sodium-meta-periodate in 5 ml 200 mM acetate buffer, pH 5.5 and stirred overnight in the dark at 4° C. The enzyme was desalted using a Sephadex G-25 column (Pharmacia PD-10 prepacked column). The resultant periodate oxidised enzyme was then stored at 4° C. and was used within 2 weeks. The graphite base electrodes were immersed in a solution of hexadecylamine in ethanol (1 mg/ml) for 15 minutes. The electrodes were removed, shaken and allowed to air dry. The dry electrodes were then placed in a solution of TTF in acetone (10 mg/ml) and left for 1 hour at room temperature, removed, shaken and allowed to air dry. Following this procedure, the electrodes were placed into the periodate-oxidised glucose oxidase solution and incubated at room temperature for 90 minutes. After removal from the enzyme solution the electrodes were immediately placed in a solution of adipic dihydrazide in 100 mM sodium acetate buffer, pH 5.5 (2.5 mg/ml) and left for 30 minutes at room temperature. The electrodes were then rinsed in distilled water and were ready for use or storage in 20 mM phosphate buffer pH 7.5 at 4° C.

Figure 10:
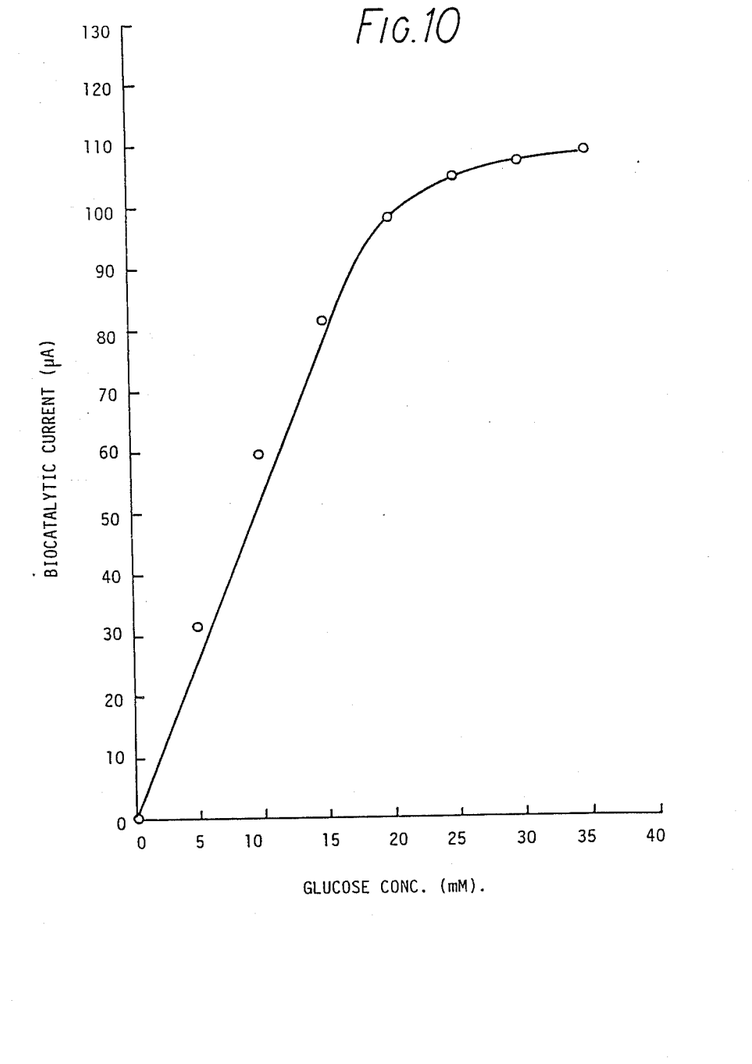
FIG. 10 is a graph showing a calibration curve of steady state current versus glucose concentration for a TTF-modified electrode on which GOD has been immobilised by an improved procedure.

As shown in FIG. 10, the electrodes gave a linear steady-state current response in the range 0–15 mM glucose. Above 15 mM the calibration curve became non-linear as the glucose concentration approached electrode saturation. The current response of the electrodes was high. The response of the electrode was rapid and comparable to that achieved with carbodiimide treated electrodes, taking 2–4 minutes to reach steady-state current, 90% of this response being reached in 60–90 seconds. The half-line decay of this electrodes' response at saturating glucose concentrations (50 mM) was ca. 5.5 hours. This was an improvement of some 3 hours over the carbodiimide treated electrodes. This method can be further improved by the use of periodate oxidised dextran to cross-link the enzyme with adipic dihydrazide.

Conclusions

Enzyme electrodes based on TTF exhibited fast electron transfer, low oxygen interference and a rapid response time with reproducible performance between electrodes. The effect of pH agrees with the other published data regarding glucose oxidase and artificial electron acceptors. See Ianiello et al., *Anal. Chem.* 53, and Aleksandrovskii et al., *Biokhimiya* 46, both cited supra. The pH optimum, however, was more marked than data presented on pH dependance of ferrocene mediated glucose oxidase electrodes (8). Preconditioned electrodes were reasonably stable and may be suitable for use in "one-shot" tests using disposable electrodes. Short term continuous use would also be possible.

These results demonstrate that TTF is a useful and versatile mediator of electron transfer between biological systems and electrodes. Biological systems may be enzymes, cell fragments, intact cells, tissues or enzyme labelled affinity reactions. TTF derivatives, such as mono- or poly-carboxylic acid derivatives or mono- or poly-amino derivatives, may be preferable to TTF itself in some circumstances; for example in providing greater solubility where the TTF is to be used in solution, or in providing side groups for linking the TTF molecule to the electrode surface, an enzyme, or both. Thus, TTF will be useful in a number of configurations which have previously been demonstrated with other mediators. These include:

(i) linking a TTF derivative such as monocarboxylic acid to an enzyme thus rendering it electrochemically active, i.e., as described by W. J. Aston et al., in *Biotechnology and Genetic Engineering Reviews*, vol. 1, pp. 89–120 (Ed. G. E. Russell), Newcastle-Upon-Tyne: Intercept Publishing, 1984;

(ii) the use of mediators for affinity assays (immunoassay, RNA probes and DNA probes) either as a soluble mediator or a derivative which is cleaved and then takes part in or activates an electrochemical reaction;

(iii) electrochemical applications such as biological fuel cells and bioelectrosynthesis of chemicals.

We claim:

1. A bioelectrochemical system comprising:
   a biological system comprising a redox system which requires electron transfer for its operation, wherein said redox system comprises an enzyme;
   an electrode; and
   a mediator for transferring electrons between said electrode and the enzyme of said redox system for operation of said redox system, characterized in that said mediator is tetrathiafulvalene, and is not complexed with an electron acceptor molecule.

2. The bioelectrochemical system of claim 1 wherein the tetrathiafulvalene is in solution.

3. The bioelectrochemical system of claim 1 wherein the tetrathiafulvalene is deposited on said electrode.

4. The bioelectrochemical system of claim 1 wherein said enzyme is an oxidoreductase enzyme and is immobilized on said electrode.

5. The bioelectrochemical system of claim 4 wherein the enzyme is a glycoenzyme immobilized on the electrode via its carbohydrate groups.

6. The bioelectrochemical system of claim 1 wherein the redox system effects the oxidation of glucose catalyzed by said enzyme which is selected from glucose oxidase and glucose dehydrogenase.

7. The bioelectrochemical system of claim 1 wherein said redox system is selected from enzymes, cell fragments, intact cells, tissues, and enzyme-labeled affinity reactions.

8. The bioelectrochemical system of claim 1 wherein said redox system effects the oxidation of an amino acid by said enzyme, and wherein said enzyme is amino acid oxidase.

9. An assay procedure for assaying a substance, comprising:
   causing the substance to participate in a redox system provided by a biological system, said redox system requiring electron transfer for its operation, wherein said redox system comprises an enzyme;
   providing an electrode;
   employing said electrode in an electrochemical cell including said redox system;
   providing tetrathiafulvalene as a mediator for transferring electrons between said electrode and the enzyme of said redox system for operation of said redox system; and
   deriving assay data from the electrode's response.

10. A procedure according to claim 9 wherein said biological system comprises a redox system selected from enzymes, cell fragments, intact cells, tissues, and enzyme-labeled affinity reactions.

11. An electrode for use in a bioelectrochemical system, said electrode consisting essentially of a conductive surface onto which a tetrathiafulvalene and an oxidoreductase enzyme are deposited, wherein said tetrathiafulvalene is not complexed with an electron acceptor.

12. An electrode according to claim 11 wherein the enzyme is a glycoenzyme and is immobilised on the conductive surface via its carbohydrate groups.

13. An electrode according to claim 11 wherein said oxidoreductase enzyme is selected from glucose oxidase, glucose dehydrogenase, and amino acid oxidase.

14. An electrode for use in a bioelectrochemical system, said electrode comprising a graphite conductive surface onto which a coating consisting essentially of tetrathiafulvalene is provided, wherein said tetrathiafulvalene is not complexed with an electron acceptor.

* * * * *